(12) United States Patent
Fillere

(10) Patent No.: US 8,934,279 B2
(45) Date of Patent: Jan. 13, 2015

(54) STACK PROCESSOR USING A FERROELECTRIC RANDOM ACCESS MEMORY (F-RAM) FOR CODE SPACE AND A PORTION OF THE STACK MEMORY SPACE

(75) Inventor: Franck Fillere, Colorado Springs, CO (US)

(73) Assignee: Cypress Semiconductor Corporation, San Jose, CA (US)

( * ) Notice: Subject to any disclaimer, the term of this patent is extended or adjusted under 35 U.S.C. 154(b) by 389 days.

(21) Appl. No.: 13/467,849

(22) Filed: May 9, 2012

(65) Prior Publication Data

US 2012/0294062 A1    Nov. 22, 2012

Related U.S. Application Data

(60) Provisional application No. 61/486,646, filed on May 16, 2011.

(51) Int. Cl.
*G11C 11/22* (2006.01)
*C12Q 1/68* (2006.01)
*G06F 9/30* (2006.01)

(52) U.S. Cl.
CPC ............... *C12Q 1/6883* (2013.01); *G06F 9/30* (2013.01); *G06F 9/30134* (2013.01); *G11C 11/22* (2013.01)
USPC ............................ 365/145; 365/148; 365/158

(58) Field of Classification Search
CPC ....................................................... G11C 11/22
USPC ........ 365/49.13, 65, 109, 117, 145, 148, 158; 257/295, E21.208, E21.663, E21.664, 257/E27.104, E29.164; 438/3
See application file for complete search history.

(56) References Cited

U.S. PATENT DOCUMENTS

| | | | |
|---|---|---|---|
| 5,890,199 A | | 3/1999 | Downs |
| 6,157,979 A | * | 12/2000 | Barnett ........................ 710/267 |
| 6,289,300 B1 | * | 9/2001 | Brannick et al. ................ 703/28 |
| 2003/0126487 A1 | * | 7/2003 | Soerensen et al. ............ 713/322 |
| 2003/0149809 A1 | * | 8/2003 | Jensen et al. .................... 710/22 |
| 2008/0077770 A1 | * | 3/2008 | Jensen et al. .................... 712/34 |
| 2008/0077820 A1 | * | 3/2008 | Jensen et al. .................. 713/500 |
| 2010/0185811 A1 | * | 7/2010 | Kwon ........................... 711/105 |
| 2010/0293342 A1 | * | 11/2010 | Morfey et al. ................ 711/154 |
| 2012/0047580 A1 | * | 2/2012 | Smith et al. ..................... 726/24 |

OTHER PUBLICATIONS

B. Paysan, "b16—A Forth Processor in an FPGA", Feb. 2, 2003, pp. 1-9.
B. Paysan, "b16-small—Less is More", EuroForth 2004 Proceedings, Jul. 9, 2006, pp. 1-8.
B. Paysan, "b16: Modern Processor Core", Apr. 29, 2005, pp. 1-29.

* cited by examiner

*Primary Examiner* — Harry W Byrne

(57) ABSTRACT

A stack processor using a ferroelectric random access memory (F-RAM) for code space and a portion of the stack memory space. By storing some of the associated stacks in complementary metal oxide semiconductor (CMOS) or other volatile memory, read/write operations to only F-RAM would be obviated. As compared to an all F-RAM stack implementation, a faster, less power consuming and faster program execution time is provided. Firmware code can also be provided that will tend to concentrate the more intensive calculations to that part of the stack that is in volatile memory and minimize POP/PUSH operations to the F-RAM portion of the stack. Moreover, since only the top of the stack is maintained in volatile memory, most of it remains in F-RAM which means the application can still benefit from the high F-RAM endurance and shorter power-down times.

13 Claims, 6 Drawing Sheets

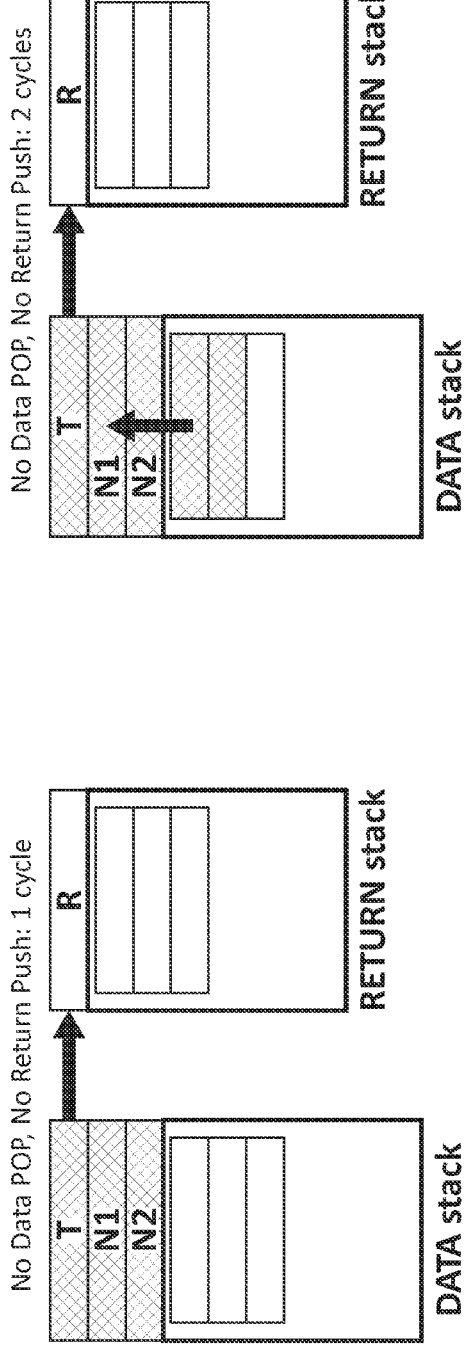
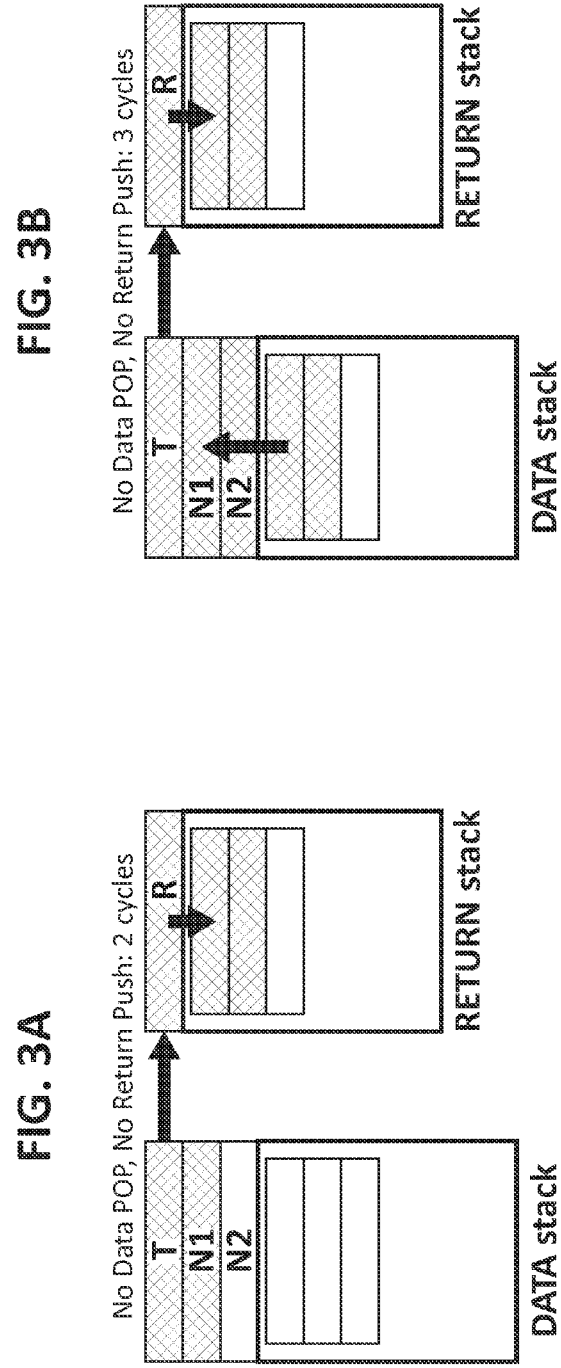
FIG. 3A
FIG. 3B
FIG. 3C
FIG. 3D

| | 00000 | 00001 | 00010 | 00011 | 00100 | 00101 | 00110 | 00111 |
|---|---|---|---|---|---|---|---|---|
| BRANCHING — Group bit 0 | NOP | RET | STOP | JMP () | JZ () | JC () | JB0 () | JB1 () |
| BRANCHING — Group bit 1 | NOP | RET | RETI | DRJNZ () | JNZ () | JNC () | JB2 () | JB3 () |

| | 01000 | 01001 | 01010 | 01011 | 01100 | 01101 | 01110 | 01111 |
|---|---|---|---|---|---|---|---|---|
| MEMORY ACCESS — Group bit 0 | LOAD | WRITE | LIT () | LIT_R () | Tpp | Rmm | T2R | R2T |
| MEMORY ACCESS — Group bit 1 | LOAD8H | WRITE8H | LOAD8L | WRITE8L | - | - | PMUL | PDIV |

| | 10000 | 10001 | 10010 | 10011 | 10100 | 10101 | 10110 | 10111 |
|---|---|---|---|---|---|---|---|---|
| LOGIC — Group bit 0 | XOR | CMPL | AND | OR | SHF_L | SHF_R | SHF_OCT | DROP_R |
| ARITH — Group bit 1 | ADD | ADDC | SUB | SUBB | SHFC_L | SHFC_R | SET_C | CLR_C |

| | 11000 | 11001 | 11010 | 11011 | 11100 | 11101 | 11110 | 11111 |
|---|---|---|---|---|---|---|---|---|
| DATA STACK — Group bit 0 | DUP | SWAP | DROP | OVER | ROT | NIP | LIT0 | LIT1 |
| BRANCHING — Group bit 1 | | | | | CALL () | | | |

*OPCODES taking an argument are marked with "()"*
*Underlined OPCODES assign the carry*

*Fig. 6*

STACK PROCESSOR USING A FERROELECTRIC RANDOM ACCESS MEMORY (F-RAM) FOR CODE SPACE AND A PORTION OF THE STACK MEMORY SPACE

RELATED APPLICATION

The present invention claims priority from U.S. Provisional Application No. 61/486,646, filed May 16, 2011, and is related to U.S. patent application Ser. No. 13/467,831, filed May 9, 2012, U.S. patent application Ser. No. 13/467,874, filed May 9, 2012, and U.S. patent application Ser. No. 13/467,816, filed May 9, 2012, the disclosures of which are herein specifically incorporated by reference in their entirety.

BACKGROUND OF THE INVENTION

The present invention relates, in general, to the field of customizable integrated circuit devices incorporating nonvolatile memory. More particularly, the present invention relates to a stack processor using a ferroelectric random access memory (F-RAM) for code space and a portion of the stack memory space.

Current nonvolatile memory technologies include, among others, electrically erasable programmable read only memory (EEPROM) and Flash memory. Despite continuing improvements to this technology, the endurance rate of Flash memory is still multiple orders of magnitude below the endurance rate of F-RAM. Therefore, for applications using Flash memory that require high endurance, some products will actually include a large Flash memory array with the associated user/program ensuring that data is stored in specific memory locations (e.g. banks of memory). Once a memory bank approaches its endurance limit, the user/program would then enable the movement of all data to a new memory bank, marking the previous memory bank as worn out and indicating it should not be used again. The typical endurance of such floating gate devices is approximately between 100,000 to 1 million write cycles.

It is also well known that writes to EEPROM and Flash is relatively slow compared to that of F-RAM. While an F-RAM write cycle is completed almost immediately, EEPROM and Flash write times take meaningfully longer. Still further, writes to an F-RAM memory cell occur at a relatively low voltage and very little current is required to change the data in the cell.

A currently implemented architecture for a stack processor is the b16 Processor described in Paysan, B., "A Forth Processor in an FPGA", Feb. 2, 2003; Paysan, B., "b16-small— Less is More", Jul. 9, 2006; and Paysan, B., "b16: Modern Processor Core", Apr. 29, 2005 and disclosed at http://www.jwdt.com/~paysan/b16.html, the disclosures of which are herein specifically incorporated by reference in their entirety. The b16 stack based processor has the top of the stacks maintained in volatile registers and the bottom of the stacks in two complementary metal oxide semiconductor (CMOS) memories. Such an architecture will lead to the possibility of the data and return stacks and code space being accessed simultaneously. Moreover, a stack processor architecture which provides for maintaining the stacks in volatile memory would cause it to suffer from very long and power demanding power-down times as the contents of a relatively large number of registers would have to be saved to nonvolatile memory on power-down. Placing some of the registers in nonvolatile Flash memory in an attempt to ameliorate this situation would, of course, lead to the endurance issues inherent in Flash. Still further, a stack processor architecture which utilizes a different memory type for code and the stacks would suffer from high power consumption peaks since all of the memories are likely to be accessed simultaneously in normal operation.

In the b16 stack processor, each 16 bit word is mapped as three, 5 bit instructions and one extra 1 bit instruction which can only be a "no operation" (NOP) or CALL. In practice this means that in the majority of cases, the fourth instruction will generally be a NOP and the instruction set is, therefore, wasting one bit per word along with a clock cycle (needed to execute the NOP) every three instructions. Still further, the b16 stack processor does not share code and data space so its architecture is even more power demanding as it can access code space and the data and return stacks all simultaneously.

SUMMARY OF THE INVENTION

Customizable integrated circuit devices will generally require the provision of some sort of processing unit on-chip to enable the device to execute different functions depending on a user defined program. One example market for customizable devices is in the field of metering functions which require higher endurance cycles than can reasonably be supplied by nonvolatile memory technologies such as Flash. Another possible market is radio frequency identification (RFID) in which low power memory cells are required.

Currently many companies also intend to develop products that operate in an environment where power supply voltage can, at times, be lost. In such applications, a need exists to be able to save current data quickly into non-volatile storage before power-down occurs.

To this end, a need also exists for an integrated circuit architecture that embodies a processor in conjunction with associated F-RAM memory. As power-down time in the event of a supply voltage disruption should be as quick as possible, it is advantageous to have as much data as possible in non-volatile memory. Stack based processors are particularly useful in such an application inasmuch as most of the registers it manipulates are in the stack.

Therefore, in using a stack-based processor, if some or all of the stacks are in F-RAM memory, most of the data is already in non-volatile memory at any given time. Even if some of the data is not already stored in F-RAM memory, the very fast write time of that memory technology also allows for the rapid back-up of the data. Moreover, such an architecture can be readily customized through the changing of the processor program allowing a wide range of potential applications such as metering functions, RFID and the like. Further, inherent in the operation of F-RAM memory is its low leakage and dynamic power requirements. The architecture disclosed herein also results in less routing congestion as there is only one code/data bus employed and it communicates with only one memory in a particular embodiment of the present invention.

In a particular embodiment of the architecture of the present invention disclosed herein the stack-based processor has all of its stacks stored in F-RAM memory. This presents the advantages of easy stack pointer management inasmuch as the stack pointer is itself a memory address. The time for saving all critical registers to memory is also minimized in that all registers are already maintained in non-volatile F-RAM per se. As previously mentioned the fast write times and low power access inherent in F-RAM provide many advantages while the use of a single, unique memory type on-chip affords easier hardware management, less intellectual property (IP) costs and also results in a smaller on-chip die area.

In accordance with another particular embodiment of the architecture of the present invention disclosed herein the stack-based processor has some, but not all, of its stacks stored in non-volatile F-RAM memory and the remainder in volatile memory. By storing some of the associated stacks in complementary metal oxide semiconductor (CMOS) or other volatile memory, read/write operations to only F-RAM would be obviated. Even though F-RAM memory requires relatively low power compared to other non-volatile memory technologies, an access to volatile memory instead could provide at least some power advantages. Further, read/write accesses to F-RAM memory only can somewhat slow down program execution and being able to access the stack memories in parallel to code execution would result in certain speed advantages. This is particularly relevant to RFID applications wherein power is only available for a relatively short, finite time when the card enters the RF field of the associated controller.

Implementing a stack processor with this type of architecture results in a compromise between an all F-RAM memory implementation providing a quicker power-down time, smaller on-chip die area and a relatively slower, more power consuming program execution versus a somewhat longer power-down time, larger on-chip die area, and a faster, less power consuming operation with a faster program execution time. Having the processor stack only partially maintained in F-RAM memory also has the advantage that, if the program compiler makes efficient use of this particular architecture, it can generate firmware code that will tend to concentrate the more intensive calculations to that part of the stack that is in volatile memory and minimize POP/PUSH operations to the F-RAM portion of the stack. Such an application will result in faster program execution through parallel access to the volatile registers which also consume less power than F-RAM memory. Moreover, since only the top of the stack is in volatile memory, most of it remains in F-RAM which means the application can still benefit from the high F-RAM endurance and shorter power-down times.

In accordance with yet another embodiment of the architecture of the present invention disclosed herein is a particular processor implementation utilizing an instruction set optimized to minimize memory fetches and thus minimize program execution time. This provides a number of distinct advantages including various low power applications and those in which the power supply is only available for a finite period of time such as RFID implementations. The use of a processor with such an optimized instruction set also allows the architecture of the present invention to be instantiated across multiple devices to support a wide range of possible operations and differing numbers of peripherals by supporting interrupts as will be more fully described hereinafter.

This particular embodiment of the present invention provides an instruction set for a stack processor architecture that is relatively small so that the associated logic is itself not too large thereby reducing current leakage and dynamic power requirements. Also disclosed is a complete set of instructions so that a multitude of possible applications can be supported with a program execution time that is not too long. Further, the instruction set disclosed is neither too complex nor too light. That is, there are not too many F-RAM memory fetches and nor is there too much logic leakage. As disclosed, the instruction set of the present invention supports the basic Forth commands as well as other operation code for generic operations while also supporting interrupts.

In accordance with still another embodiment of the architecture of the present invention disclosed herein is a particular method of operation which minimizes processor stack accesses when the associated stack is only partially implemented in F-RAM memory. The minimization of F-RAM stack accesses in conjunction with the particular processor described and disclosed herein results in less power being consumed as well as overall faster program execution as would be the case were all of the stack held in non-volatile F-RAM memory, in which instance the code could not be read while accessing the F-RAM stack.

Specifically disclosed herein is an integrated circuit device which comprises a stack processor which includes a processor core and an interrupt controller. A non-volatile memory is coupled to the processor core for storing program code and at least a portion of the stack memory space and a volatile memory is also coupled to the processor core for storing another portion of the stack memory space. The non-volatile memory may comprise ferroelectric random access memory and the volatile memory may comprise complementary metal oxide semiconductor memory with the top of the data and return stacks being maintained in CMOS and the lower portions in F-RAM.

BRIEF DESCRIPTION OF THE DRAWINGS

The aforementioned and other features and objects of the present invention and the manner of attaining them will become more apparent and the invention itself will be best understood by reference to the following description of a preferred embodiment taken in conjunction with the accompanying drawings, wherein:

FIGS. 3A through 3D inclusive are exemplary illustrations of an instruction for the copying of the top of the data stack ("T") into the top of a return stack ("R");

FIG. 6 is an exemplary table of possible operating code mappings for the Forth core of the preceding FIGS. 1 and 2.

DESCRIPTION OF A REPRESENTATIVE EMBODIMENT

Figure 1:
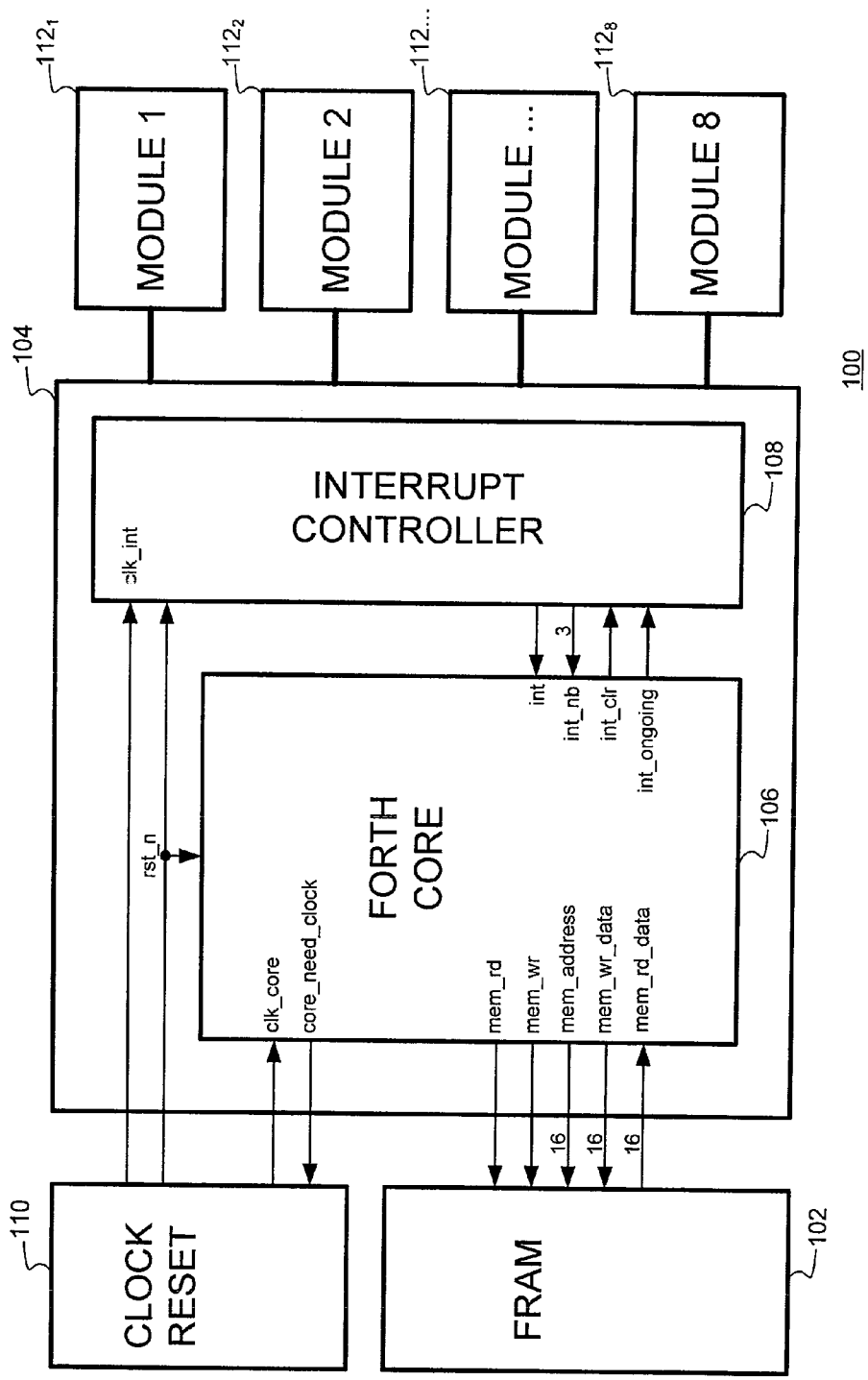
FIG. 1 is a functional block diagram of a stack processor using a ferroelectric random access memory (F-RAM) for both code and data space in accordance with a particular representative embodiment of the present invention.

With reference now to FIG. 1, a functional block diagram of a stack processor 100 using a ferroelectric random access memory (F-RAM) for both code and data space in accordance with a particular representative embodiment of the present invention is shown. The stack processor 100 comprises, in pertinent part, an F-RAM memory array 102 and associated processor 104. The F-RAM memory array 102 may be of the type provided by Ramtron International Corporation, Colorado Springs, Colo., assignee of the present invention. The processor 104, as shown, may comprise a Forth core 106 developed by Ramtron International Corporation, assignee of the present invention.

An associated interrupt controller 108 forms a portion of the processor 104 which also operates in conjunction with a clock reset circuit 110 as shown. In the representative embodiment illustrated, eight modules (Module 1 through Module 8) respectively labeled as 112$_1$ through 112$_8$ inclusive are associated with the stack processor 100. A single code/data bus couples the Forth core 106 to the F-RAM memory array 102 and comprises memory read and write lines (mem_rd, mem_wr) and 16 bit memory address, memory write data and memory read data buses (mem_address, mem_wr_data, mem_rd_data) buses as illustrated.

The clock reset circuit 110 provides a clock interrupt signal (clk_int) to the interrupt controller 108 as well as a reset n (rst_n) signal to both the Forth core 106 and interrupt controller 108. The clock reset circuit 110 also provides a core clock signal (clk_core) to the Forth Core 106 and receives a core_need_clock therefrom. The interrupt controller 108 provides an interrupt signal (int) and a 3 bit int_nb signal to the Forth core 106 and receives an interrupt clear (int_clr) and ongoing interrupt (int_ongoing) signals therefrom.

Figure 2:
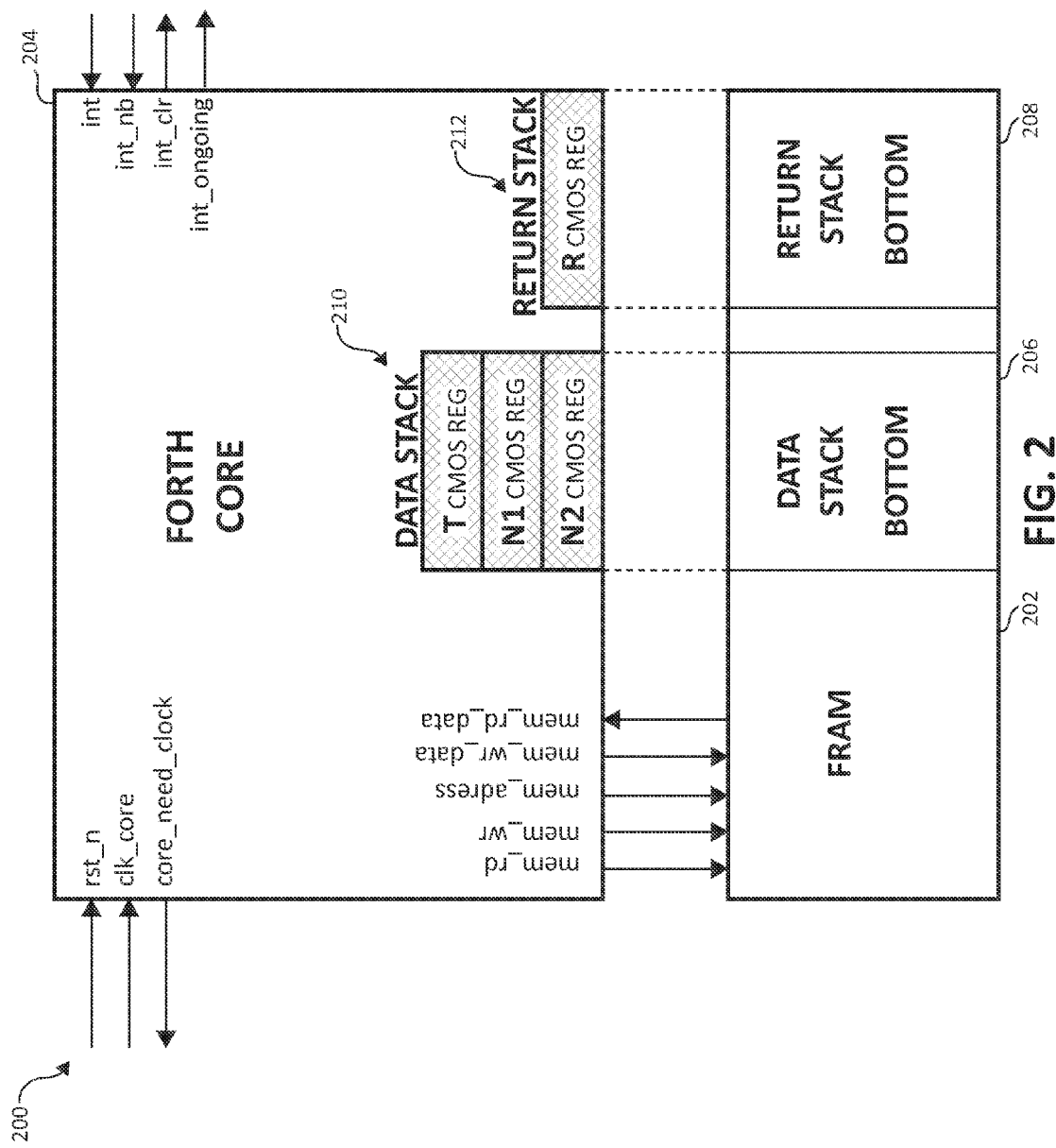
FIG. 2 is a follow-on functional block diagram of a portion of a stack processor utilizing both F-RAM and CMOS memory in accordance with another particular representative embodiment of the present invention.

With reference additionally now to FIG. 2, a follow-on functional block diagram of a portion of a stack processor 200 utilizing both F-RAM and CMOS memory in accordance with another particular representative embodiment of the present invention is shown. As indicated, there is only one processor code/data bus, and it goes to the F-RAM memory array 202 only. The stack processor 200 comprises a Forth Core 204 having a data stack 210 and a return stack 212 while the F-RAM memory array 202 has a corresponding data stack bottom 206 and a return stack bottom 208.

In this figure the organization of an embodiment of the stack processor 200 is shown. The data stack 210 has its top part in the processor core 204 in volatile CMOS registers in this case. The bottom of the data stack 206 is in the nonvolatile F-RAM memory array 202. In the same manner, the top of the return stack 212 is in the processor core 204 in volatile CMOS registers 212 and the bottom of the return stack 208 is in the F-RAM memory array 202. Therefore, if a program only needs to modify the top of the data stack with no push/pop to the F-RAM memory array 202 stack, only CMOS register accesses will be involved. This would result in overall lower power consumption. If a power down were to occur, there would then only be the contents of a very limited number of CMOS registers to save before a power loss occurs.

It should be noted that a portion of the performance of this particular stack processor 200 implementation is due to the instruction set. However, some of it also results from the fact that the program is relatively small and can be written to derive benefit from the top of the stacks being in CMOS registers.

With reference additionally now to FIGS. 3A through 3D inclusive, exemplary illustrations of an instruction for the copying of the top of the data stack ("T") into the top of a return stack ("R") are shown.

The proposed stack access method illustrated maintains track of the where the stack pointer is relative to the boundary between the CMOS and F-RAM portions of the stack. As illustrated, a data transfer between the data and return stacks can result in four possible initial configurations. The shaded boxes indicate that there is valid data in this stack memory address.

In FIG. 3A, the data AND return stack have not passed the F-RAM boundary. In FIG. 3B, the data stack ONLY has passed the F-RAM boundary. In FIG. 3C, the return stack ONLY have passed the F-RAM boundary and in FIG. 3D, both the data and return stack have passed the F-RAM boundary As can be seen, according to the specific configuration, the proposed algorithm performs or does not perform a stack pop/push and for the specific instruction outlined above, the algorithm would do the following:

As shown in FIG. 3A, copy T into R; as shown in FIG. 3B, POP the data stack and copy T into R; as shown in FIG. 3C, PUSH the return stack and copy T into R; and as shown in FIG. 3D, PUSH the return stack, POP the data stack and copy T into R. In this manner, only a minimum number of F-RAM memory array accesses are required.

Figure 4:
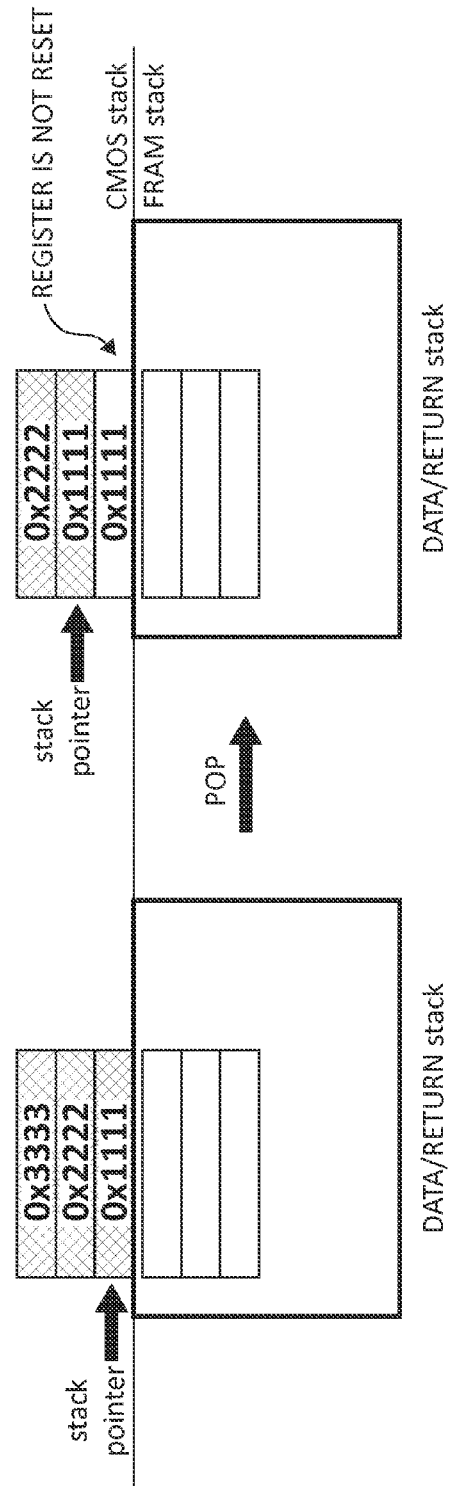
FIG. 4 is an exemplary illustration of a method in accordance with the representative embodiment of the present invention illustrated in FIG. 2 wherein the CMOS registers are only updated when required and unused portions of the CMOS stack are not updated to conserve power.

With reference additionally now to FIG. 4, an exemplary illustration of a method in accordance with the representative embodiment of the present invention illustrated in FIG. 2 is shown wherein the CMOS registers are only updated when required and unused portions of the CMOS stack are not updated to conserve power. In this implementation of the present invention, the third CMOS register bus of the stack has not been updated or reset and since it is now in the unused part of the stack its current value is "don't care". As can be determined, not updating that register bus allows for the saving of some more power.

Figure 5:
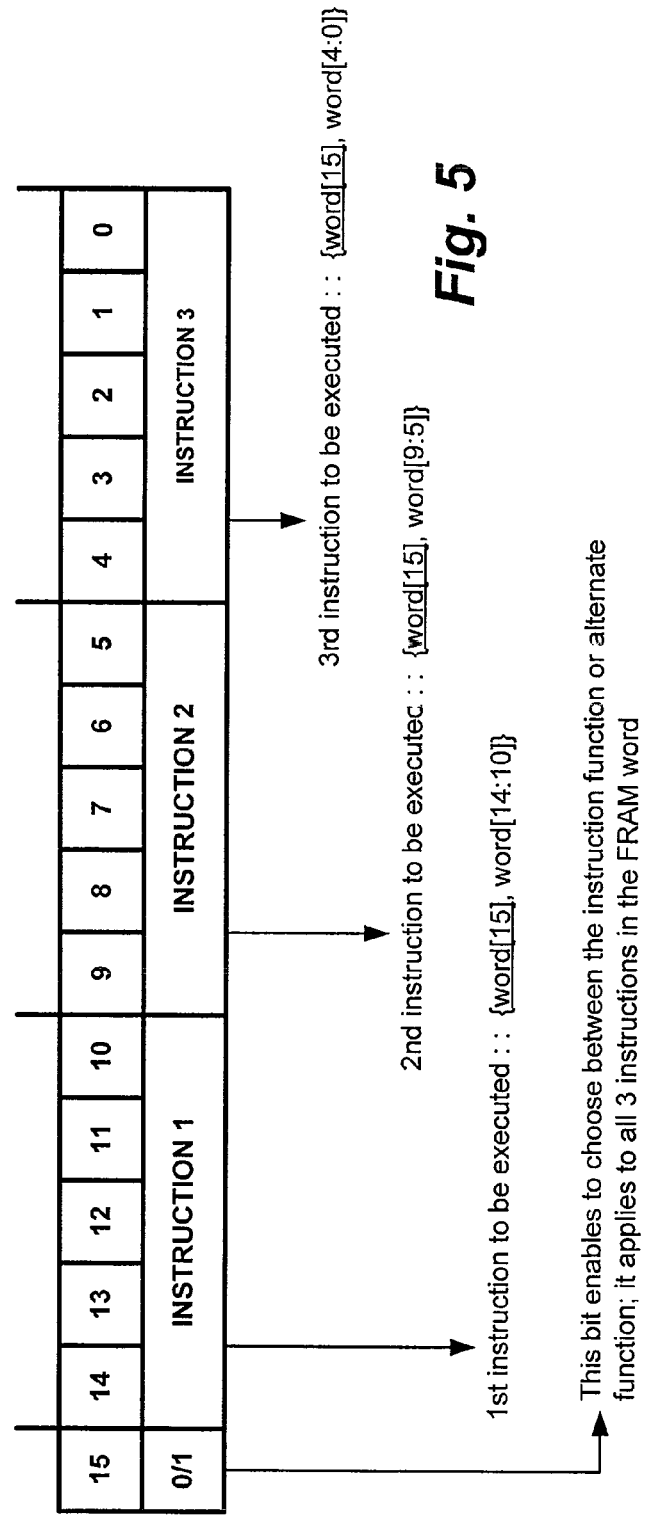
FIG. 5 is an exemplary illustration of a 16 bit instruction set in accordance with a particular embodiment of the present invention which has been optimized to minimize memory fetches.

With reference additionally now to FIG. 5, an exemplary illustration of a 16 bit instruction set in accordance with a particular embodiment of the present invention is shown which has been optimized to minimize memory fetches.

In this particular implementation of the present invention, the disclosed instruction set is based on a 16 bit memory code space. In order to determine the appropriate instruction set, the following possibilities may be examined:

any 4 bit instruction (or less) set would allow up to 16 instructions (or less) and so would not be sufficient as the program would take too long to execute with too many F-RAM memory array fetches;

any 7 bit instruction set (or more) would require 128 instructions or more, so too much leakage/dynamic power would be required and the logic would be excessively large;

a 6 bit instruction set would require 64 instructions, which while sufficient, is nonetheless very difficult to map into a 16-bit word without wasting too many bits;

a 5 bit instruction set would require 32 instructions and would appear to be a bit too limiting.

As can be seen in the exemplary instruction set illustrated, 64 instructions can be provided while minimizing the waste of memory bits. The 16 bit word MSB is a bit used by each instruction, therefore each instruction is 6 bits wide (which gives a total of 64 instructions maximum). As a consequence, the full 16 bits of code are used.

With reference additionally now to FIG. 6, an exemplary table of possible operating code ("opcode") mappings for the Forth core of the preceding FIGS. 1 and 2 is shown. As illustrated, the Forth core instructions are grouped by the categories of: Branching, Memory Access, Logic, Arithmetic and Data Stack and those opcodes are shown which share the same five lower significant bits and differ only by the one most significant group bit as shown in the preceding FIG. 5.

While there have been described above the principles of the present invention in conjunction with specific circuitry and technology, it is to be clearly understood that the foregoing description is made only by way of example and not as a limitation to the scope of the invention. Particularly, it is recognized that the teachings of the foregoing disclosure will suggest other modifications to those persons skilled in the relevant art. Such modifications may involve other features which are already known per se and which may be used instead of or in addition to features already described herein. Although claims have been formulated in this application to particular combinations of features, it should be understood that the scope of the disclosure herein also includes any novel feature or any novel combination of features disclosed either explicitly or implicitly or any generalization or modification thereof which would be apparent to persons skilled in the relevant art, whether or not such relates to the same invention as presently claimed in any claim and whether or not it mitigates any or all of the same technical problems as confronted by the present invention. The applicants hereby reserve the right to formulate new claims to such features and/or combinations of such features during the prosecution of the present application or of any further application derived therefrom.

As used herein, the terms "comprises", "comprising", or any other variation thereof, are intended to cover a non-exclusive inclusion, such that a process, method, article, or apparatus that comprises a recitation of certain elements does not necessarily include only those elements but may include other elements not expressly recited or inherent to such process, method, article or apparatus. None of the description in the present application should be read as implying that any particular element, step, or function is an essential element which must be included in the claim scope and THE SCOPE OF THE PATENTED SUBJECT MATTER IS DEFINED ONLY BY THE CLAIMS AS ALLOWED. Moreover, none of the appended claims are intended to invoke paragraph six of 35 U.S.C. Sect. 112 unless the exact phrase "means for" is employed and is followed by a participle.

What is claimed is:

1. An integrated circuit device comprising:
   a stack processor comprising a processor core and an interrupt controller;
   a non-volatile memory coupled to said processor core for storing program code and at least a portion of the stack memory space; and
   a volatile memory coupled to said processor core for storing another portion of said stack memory space.

2. The integrated circuit device of claim 1 wherein said volatile memory comprises complementary metal oxide semiconductor memory.

3. The integrated circuit device of claim 1 further comprising:
   a clock circuit coupled to said processor core and said interrupt controller for providing a clock signal thereto.

4. The integrated circuit device of claim 1 further comprising:
   a reset circuit coupled to said processor core and said interrupt controller for providing a reset signal thereto.

5. The integrated circuit device of claim 1 further comprising:
   at least one module coupled to said stack processor.

6. The integrated circuit device of claim 1 wherein said non-volatile and volatile memories receive read and write commands from said processor core.

7. The integrated circuit device of claim 6 wherein said non-volatile and volatile memories additionally receive address commands from said processor core.

8. The integrated circuit device of claim 7 wherein said non-volatile and volatile memories write data to memory locations indicated by said address commands from said processor core in response to said write commands.

9. The integrated circuit device of claim 7 wherein said non-volatile and volatile memories read data from memory locations indicated by said address commands from said processor core in response to said read commands.

10. The integrated circuit device of claim 1 wherein a portion of at least one data stack of said processor core is stored in said non-volatile memory.

11. The integrated circuit device of claim 10 wherein said portion of said at least one data stack is a bottom portion and a top portion is stored is stored in said volatile memory.

12. The integrated circuit device of claim 1 wherein at least one return stack of said processor core is stored in said non-volatile memory.

13. The integrated circuit device of claim 12 wherein said portion of said at least one return stack is a bottom portion and a top portion is stored in said volatile memory.

* * * * *